United States Patent
Bonanni et al.

(10) Patent No.: US 9,256,935 B2
(45) Date of Patent: Feb. 9, 2016

(54) MAPPING TRANSFER FUNCTION FOR AUTOMATED BIOLOGICAL SAMPLE PROCESSING SYSTEM

(71) Applicant: General Electric Company, Schenectady, NY (US)

(72) Inventors: Pierino Gianni Bonanni, Loudonville, NY (US); Weston B. Griffin, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 185 days.

(21) Appl. No.: 14/095,347

(22) Filed: Dec. 3, 2013

(65) Prior Publication Data

US 2015/0154748 A1  Jun. 4, 2015

(51) Int. Cl.
| | |
|---|---|
| G06T 7/00 | (2006.01) |
| G01N 1/28 | (2006.01) |
| G01N 35/00 | (2006.01) |
| G01N 35/04 | (2006.01) |

(52) U.S. Cl.
CPC .......... *G06T 7/0012* (2013.01); *G01N 1/28* (2013.01); *G01N 1/286* (2013.01); *G01N 35/0099* (2013.01); *G01N 35/00594* (2013.01); *G01N 35/04* (2013.01); *G01N 2001/282* (2013.01); *G01N 2001/288* (2013.01); *G01N 2035/0493* (2013.01); *G06T 2207/30072* (2013.01)

(58) Field of Classification Search
None
See application file for complete search history.

(56) References Cited

U.S. PATENT DOCUMENTS

| | | | |
|---|---|---|---|
| 4,294,544 A | 10/1981 | Altschuler et al. | |
| 5,460,057 A | 10/1995 | Østrup | |
| 5,641,682 A * | 6/1997 | Pagels et al. | 436/43 |
| 5,925,569 A | 7/1999 | Gorog et al. | |
| 6,089,715 A | 7/2000 | Hoover et al. | |
| 6,997,305 B2 | 2/2006 | Demarest et al. | |
| 2003/0017446 A1 | 1/2003 | Chasse et al. | |

(Continued)

FOREIGN PATENT DOCUMENTS

| | | | |
|---|---|---|---|
| WO | 01/31317 A1 | 5/2001 | |
| WO | WO 0131317 A1 * | 5/2001 | G01N 21/00 |
| WO | 2012146770 A1 | 11/2012 | |

OTHER PUBLICATIONS

PCT International Search Report and Written Opinion from corresponding PCT Application No. PCT/EP2014/074669 dated Jan. 21, 2015.

*Primary Examiner* — Utpal Shah
*Assistant Examiner* — Mai Tran
(74) *Attorney, Agent, or Firm* — John P. Darling (57) ABSTRACT

A gripping element may be commanded to move to predetermined robot-frame locations, and markings may be punched into a calibration sample capture substrate at each location. A calibration image may be obtained, and fiducial markings on the gripping element may be detected. A set of calibration regions of interest may be predicted, and the previously punched markings may be detected. A sampling system may then create a mapping transfer function between detected image locations and real-world locations resulting from the commanded locations of the gripping element when the markings were punched. An indication may subsequently be received that a biological sample capture substrate is ready to be processed. An image of the sample capture substrate may be obtained, and the fiducial markings may be detected. Based on those image locations and the mapping transfer function, biological sample portions may be automatically taken from the sample capture substrate.

18 Claims, 10 Drawing Sheets

(56) References Cited

U.S. PATENT DOCUMENTS

| | | |
|---|---|---|
| 2004/0014228 A1 | 1/2004 | Brignac, Jr. et al. |
| 2004/0085443 A1* | 5/2004 | Kallioniemi et al. ......... 348/135 |
| 2006/0199169 A1 | 9/2006 | Lam et al. |
| 2008/0242978 A1 | 10/2008 | Simon et al. |
| 2009/0048510 A1 | 2/2009 | Miller et al. |
| 2012/0038905 A1* | 2/2012 | Balbuena ..................... 356/71 |
| 2013/0091176 A1 | 4/2013 | Harris et al. |

* cited by examiner

MAPPING TRANSFER FUNCTION FOR AUTOMATED BIOLOGICAL SAMPLE PROCESSING SYSTEM

BACKGROUND

Porous substrates may be used to facilitate the capture, stabilization, and storage of biological fluid samples. Pharmaceutical research involving blood testing, and forensic analysis of biological fluids collected using buccal swabs, are two examples in which substrates may be employed as a vehicle for the stabilization and storage of DNA. Such substrates may improve the long term stability of the DNA at room temperature and facilitate integration with an automated workflow. To process a sample deposited on a substrate, a portion of the substrate containing the sample is separated from the substrate (e.g., punched out). The punched out portion may be added to reagents and analyzed. It may be important to accurately locate the punch on the substrate (e.g., in case another punch needs to be taken from the same sample in the future). Moreover, the number of samples, such as DNA samples, that are being sent to forensic DNA data banking labs is increasing, and it would therefore be desirable to provide systems and methods to facilitate an automated processing of biological samples in an accurate and consistent manner.

DETAILED DESCRIPTION

In the following detailed description, numerous specific details are set forth in order to provide a thorough understanding of embodiments. However it will be understood by those of ordinary skill in the art that the embodiments may be practiced without these specific details. In other instances, well-known methods, procedures, components and circuits have not been described in detail so as not to obscure the embodiments.

Figure 1:
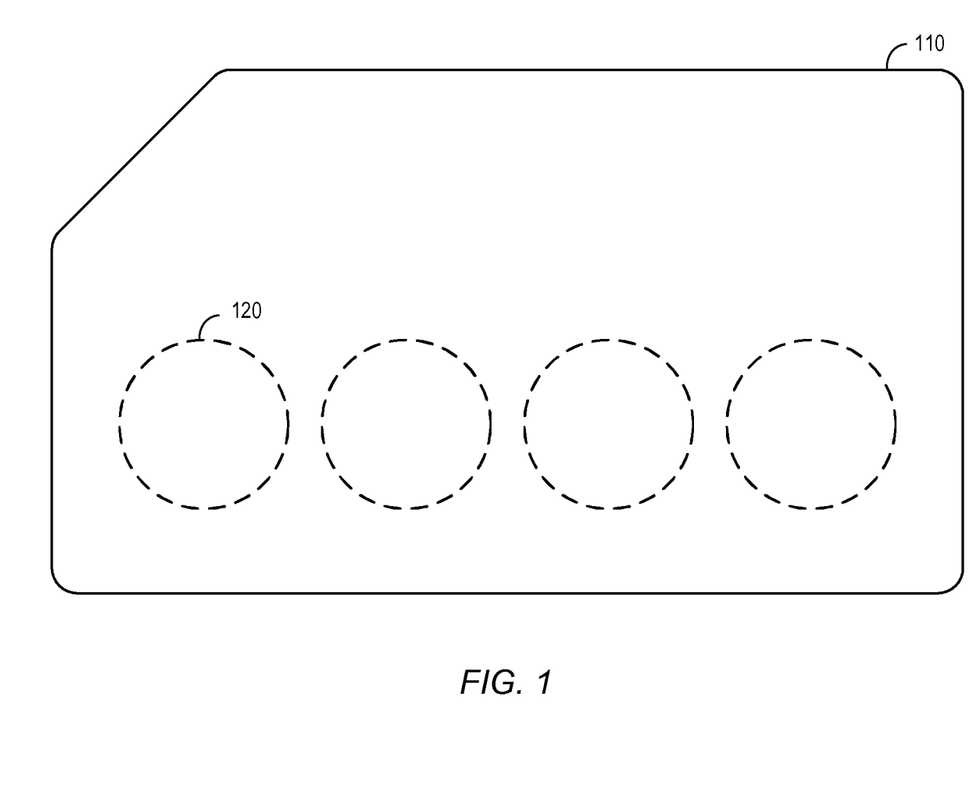
FIG. 1 is a schematic block diagram of a biological sample capture substrate.

FIG. 1 is a schematic block diagram of a biological fluid sample capture substrate 110. As used herein, the phrase "biological fluid" may refer to, for example, blood, saliva, plant material, insect material, viral material, bacterial material, genetic material, food, animal biological fluid, or genetic material. In some cases, the sample capture substrate 110 includes indicia 120, such as a circle printed in ink to help identify where on the substrate a collector should deposit a biological fluid sample. In the example of FIG. 1, the substrate 1100 may be used to collect four biological fluid samples (one sample being placed in each of the dotted-line circles comprising the indicia 120). Note, however, that different substrates 110 may be able to collect any number of biological fluid samples. One example of biological fluid sample capture substrates 110 are Fast Technology for Analysis ("FTA") cards that may be used, for example, to collect and isolate nucleic acid samples for analysis. According to some embodiments, the substrate 110 may be composed of a material that stabilizes and/or protects nucleic acids from degradation at room temperature.

Figure 2:
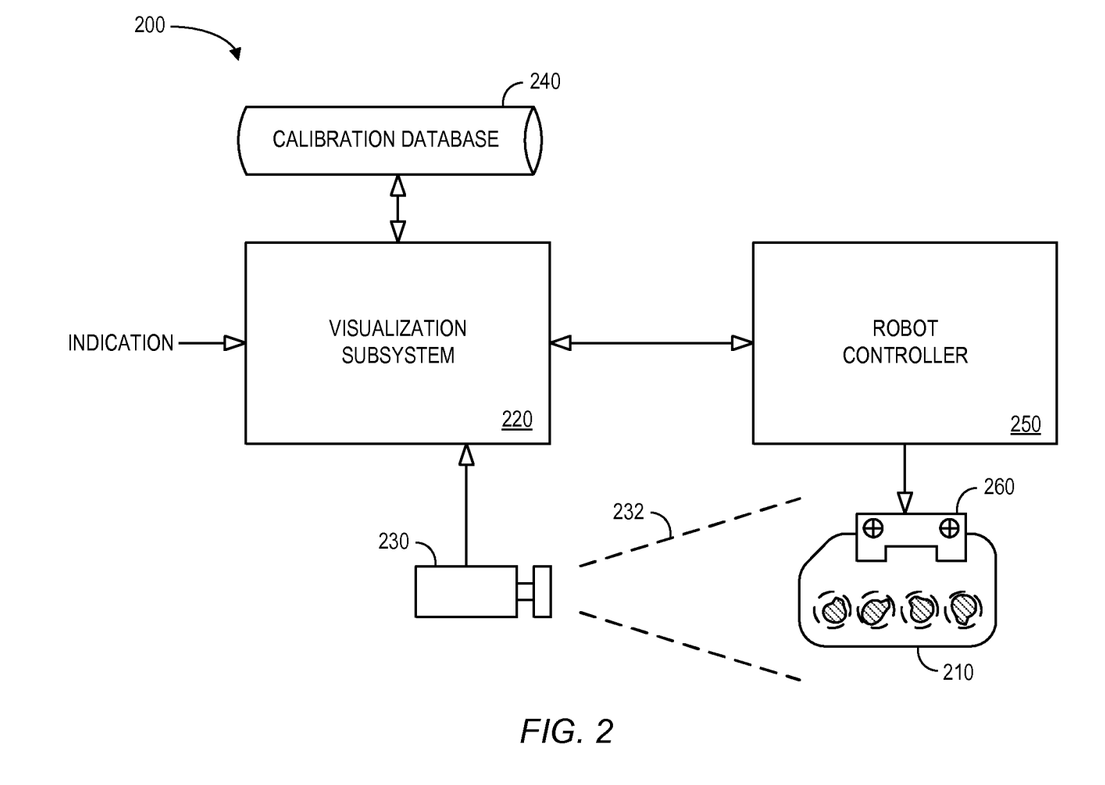
FIG. 2 is a high-level architecture of a system in accordance with some embodiments.

FIG. 2 is a high-level architecture of an automated biological processing system 200 that may be used to analyze a sample capture substrate 210 in accordance with some embodiments. The system 200 includes a visualization subsystem 220 having a camera 230 able to capture image information within a field of view 232. The system 200 also includes a robot controller 250 in communication with the visualization subsystem 220 that may use a gripping element 260 to pick up the sample capture substrate 210 (e.g., from a holder that contains multiple substrates 210) and move the substrate 210 into the field of view 232 of the camera 230.

According to some embodiments, the "automated" biological processing system 200 may receive an indication that that substrate 210 is ready to be processed. The indication may be received, for example, from a lab technician via a Graphical User Interface ("GUI") or be automatically generated (e.g., directly by the robot controller or when the visualization subsystem 220 determines that the substrate 210 is ready). As used herein, the term "automated" may refer to, for example, actions that can be performed with little or no human intervention.

As used herein, devices, including those associated with the system 200 and any other device described herein, may exchange information via any communication network which may be one or more of a Local Area Network (LAN), a Metropolitan Area Network (MAN), a Wide Area Network (WAN), a proprietary network, a Public Switched Telephone Network (PSTN), a Wireless Application Protocol (WAP) network, a Bluetooth network, a wireless LAN network, and/or an Internet Protocol (IP) network such as the Internet, an intranet, or an extranet. Note that any devices described herein may communicate via one or more such communication networks.

The visualization subsystem 220 may store information into and/or retrieve information from a calibration database 240. The calibration database 240 may be locally stored or reside remote from the system 200. Although a single visualization subsystem 220 and robot controller 250 are shown in FIG. 2, any number of such devices may be included. Moreover, various devices described herein might be combined according to embodiments of the present invention. For example, in some embodiments, the visualization subsystem 220 and the robot controller 250 might comprise a single apparatus.

Figure 3:
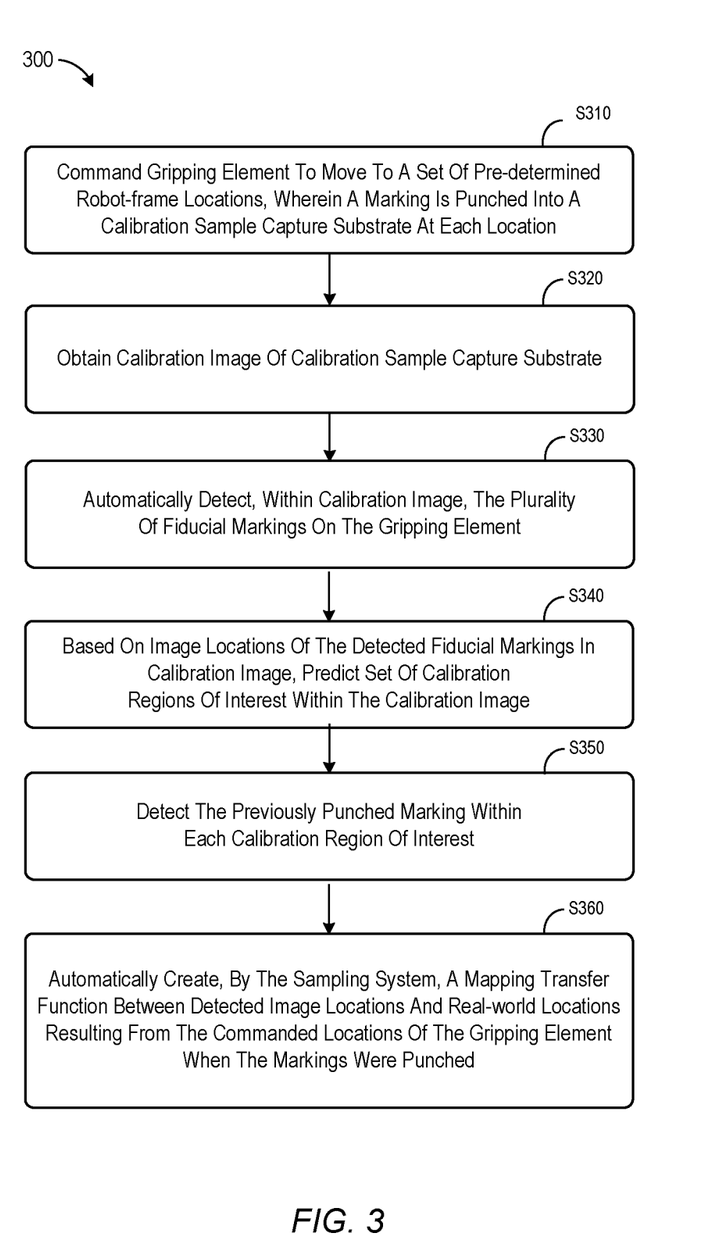
FIG. 3 illustrates a calibration method that might be performed according to some embodiments.

The system 200 may facilitate automated separation of substrate portions (e.g., punches) containing biological samples in an efficient and accurate manner in accordance with any of the embodiments described herein. For example, FIG. 3 illustrates a calibration method 300 that might be performed by some or all of the elements of the system 200 described with respect to FIG. 2. The flow charts described herein do not imply a fixed order to the steps, and embodiments of the present invention may be practiced in any order that is practicable. Note that any of the methods described herein may be performed by hardware, software, or any combination of these approaches. For example, a computer-readable storage medium may store thereon instructions that when executed by a machine result in performance according to any of the embodiments described herein.

Note that the method 300 may be associated with an automated biological sampling system having a gripping element to hold sample capture substrates. For example, the gripping element might comprise a movable clamp or jaw, controlled by a robot controller, capable of holding and moving an FTA card. At S310, the gripping element is commanded to move to a set of pre-determined robot-frame locations. Moreover, a marking is punched into a calibration sample capture substrate at each location. For example, the gripping element might be commanded to grab a blank FTA card and punch a three-by-three matrix of holes into the card.

At S320, a calibration image of the calibration sample capture substrate may be obtained. Consider, for example, FIG. 4 which illustrates 400 a capture substrate 410 being held by a gripping element 460. The capture substrate 410 includes a set of markings 412 that were created without modification of the grasp of the capture substrate prior to acquisition of the calibration image. In the illustration 400 of FIG. 4, the markings 412 are a three-by-three matrix of holes that were previously punched through the calibration sample capture substrate 410. At S320, a camera may obtain a calibration image of capture substrate 410 and gripping element 460.

At S330, a plurality of fiducial markings on the gripping element may be automatically detected within the calibration image. The fiducial markings may comprise, for example, a logo, crosshairs, or any other pre-determined detectable feature (including Light Emitting Diodes (LEDs) or markings that are outside of the visual spectrum). Referring again to FIG. 4, note that the gripping element 460 includes two fiducial markings 462 (crosshairs) that may be detected (e.g., via pattern matching) within an image captured by a camera. Moreover, note that the gripping element 460 might be offset 422 from a perfect horizontal orientation and/or the substrate 410 might be offset with respect to the gripping element 460, resulting in an overall offset 424 of the substrate 410.

Referring again to FIG. 3, at S340, a set of calibration regions of interest within the calibration image may be predicted based on image locations of the detected fiducial markings. In the illustration 400 of FIG. 4, the detected crosshair markings 462 may be used to predict a region of interest 420. That is, the locations and/or orientations of the crosshair markings 462 may be used to predict the region of interest 420 where one of the nine markings 412 are likely to be found. Note that nine such regions of interest 420 might be predicted in the illustration 400 of FIG. 4.

Figure 4:
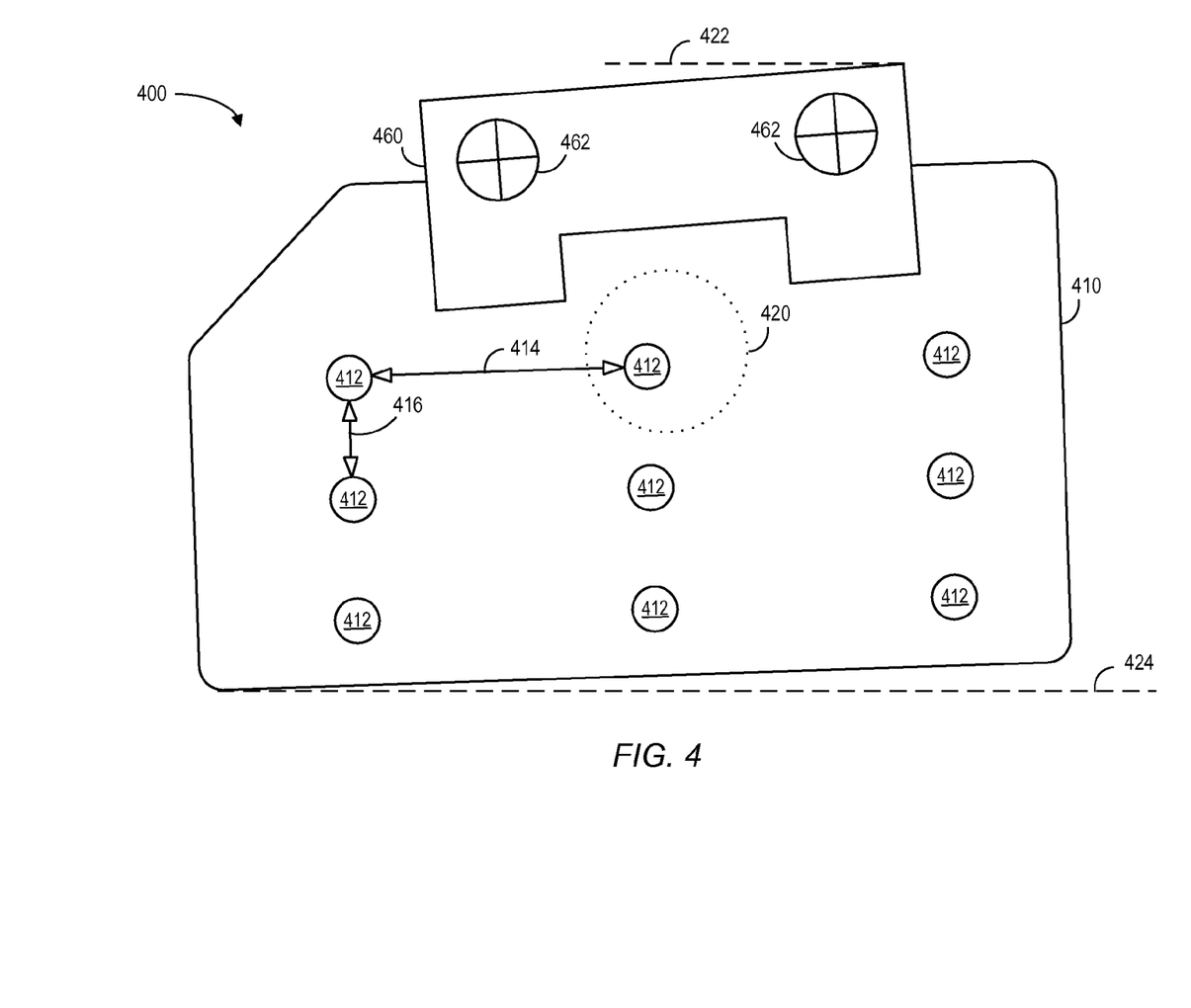
FIG. 4 is a calibration example associated with some embodiments.

At S350, one of the markings previously created on the sample capture substrate may be detected within each of the calibration regions of interest. For example, an image processing software application might examine each region of interest looking for a punched hole or other calibration marking. At S360, the sampling system may automatically create a mapping transfer function between detected image locations and real-world locations resulting from the commanded locations of the gripping element when the markings were punched (e.g., at S310). In the illustration of FIG. 4, the detected locations and relative orientations of the fiducial markings and the three-by-three matrix of punched holes 412, having known horizontal separations 414 and vertical separations 416, could be used to create such a mapping function. The mapping function may then be stored (e.g., in a calibration database) and later used to adjust and improve the automated processing to isolate sample portions from the capture substrate.

Figure 5:
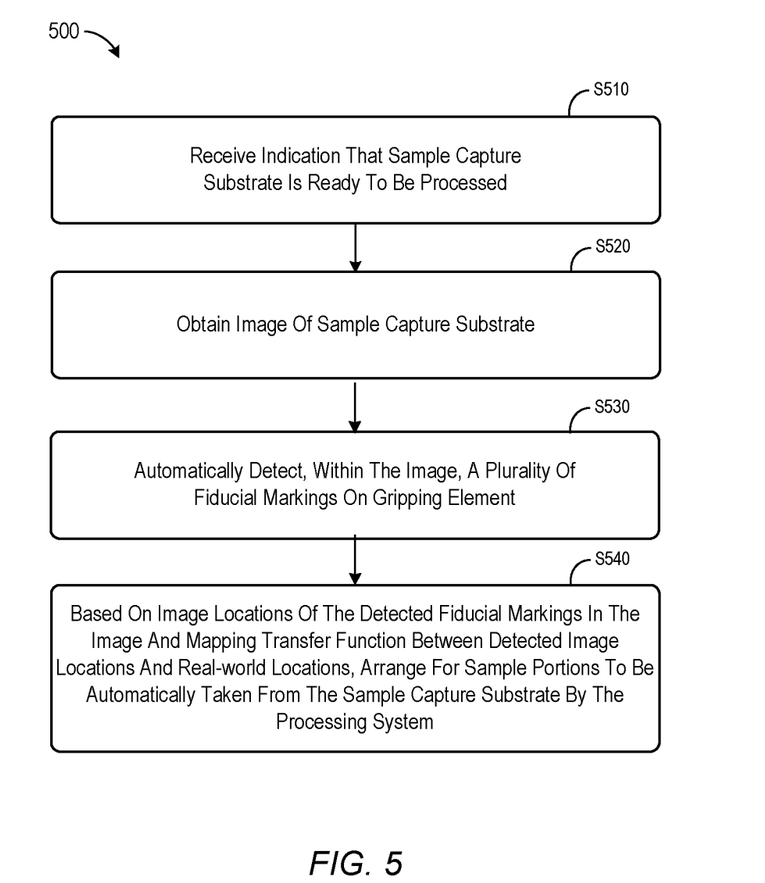
FIG. 5 illustrates a processing method that might be performed according to some embodiments.

FIG. 5 illustrates a sample portion isolation method 500 that might be performed according to some embodiments. At S510, an indication that a sample capture substrate is ready to be processed for acquisition of a sample portion may be received. For example, a lab technician might select an icon on a GUI or press a button to indicate that an FTA card is ready to be processed. According to some embodiments, the indication may be automatically generated by a visualization subsystem or a robot controller.

At S520, an image of the sample capture substrate may be obtained. At S530, a plurality of fiducial markings on a gripping element may be automatically detected within the image. Consider, for example, FIG. 6 which is an illustration of a representative image 600 of a capture substrate with a plurality of applied samples 620 associated with some embodiments. In particular, an FTA card 610 having samples 620 is held by a gripping element 660. Moreover, the gripping element 660 contains two crosshair fiducial markings 662 that may be automatically detected in the image.

At S540, based on image locations of the detected fiducial markings in the image and a mapping transfer function between detected image locations and real-world locations, it may be arranged for sample portions to be automatically taken from the sample capture substrate by the processing system. In some embodiments, information about the detected fiducial markings in the image may be used to adjust/correct a pre-stored mapping transfer function to create a new mapping to robot-frame locations that may be used when arranging for the sample portions to be taken. According to some embodiments, this arranging includes transmitting location information from a visualization subsystem to a robot controller associated with the gripping element. The robot controller may, for example, facilitate the punching of a plurality of sample portions, separating the portion from the sample capture substrate.

The calibration method described with respect to FIG. 3 and the processing method described with respect to FIG. 5 may facilitate the determination of a real-world location of the fiducial markings and develop a mapping function between the image and real-world coordinates to account for various kinds of image distortion and positioning variations between the robot and the punching system. Once that is done, features of interest (e.g., samples) may be located in accordance with the fiducial markings in the image, even when the camera has been slightly moved or bumped (causing an in-plane translation or rotation). Note that one could instead take an image of the card and punch the locations without calibrating and/or using fiducials on the gripper. However, because integration of the camera directly into the punching system would be difficult, embodiments described herein may allow the camera to be at a different location yet robustly (and more simply) maintain the punching accuracy necessary by using the gripper-relative fiducial. One could calibrate the camera relative to the entire robot coordinate system, but if the camera station or punching station is moved or bumped, a significant teaching effort would be required to recalibrate the three systems. Embodiments described herein may simplify this by using an approximate positioning of punching system and the camera system relative to the robot. With the calibration grid punching and the gripper fiducials described herein, the calibration can be associated with a relatively simple processing (calibration) routine. Note that a certain degree of repeatability may be provided when moving from the image location to the punching system, but the repeatability could be lower when moving the card from a storage location to the image location (which is more likely to be a larger move).

Figure 6:
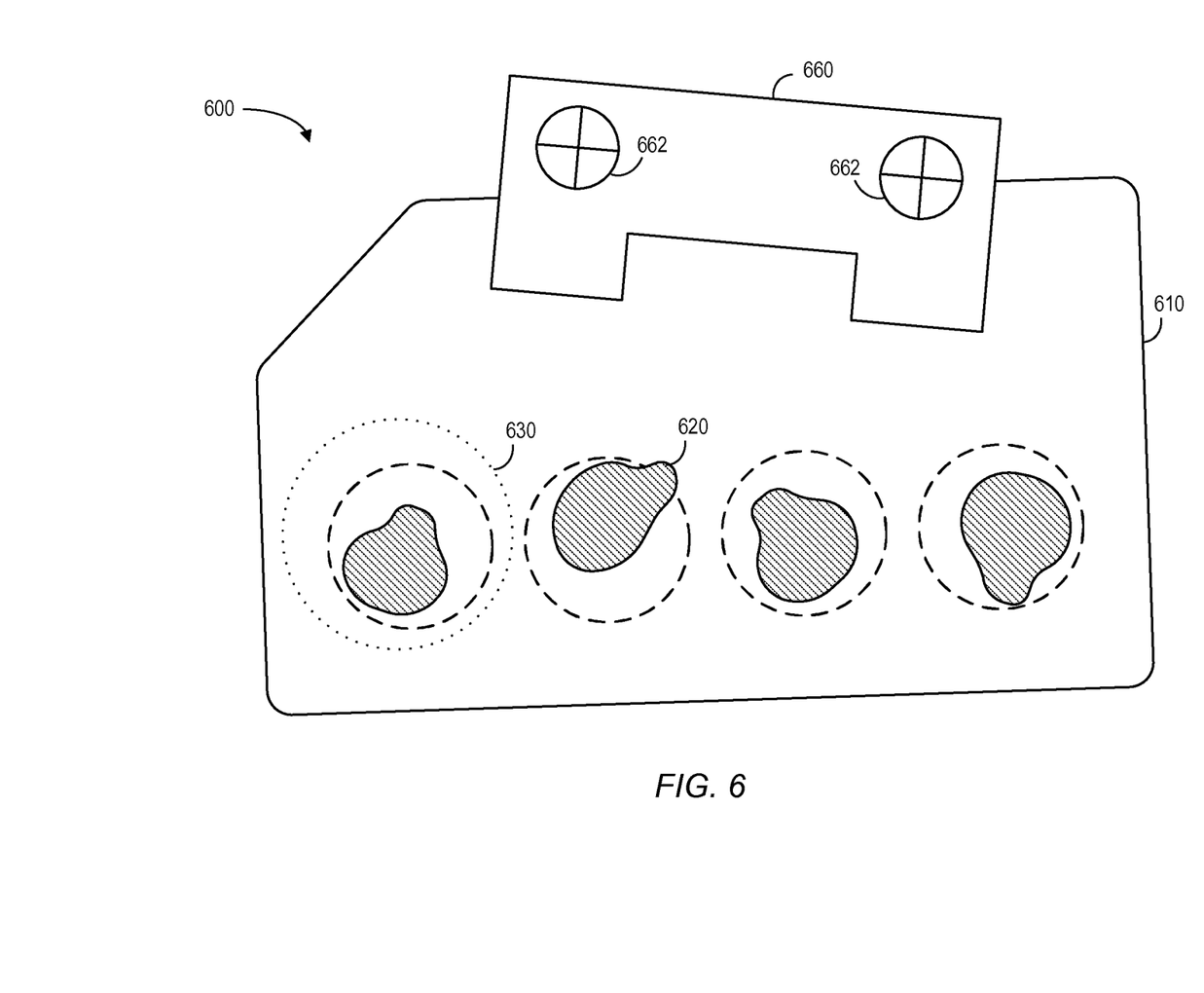
FIG. 6 is an illustration of a representative image of a capture substrate with a plurality of applied samples associated with some embodiments.
Figure 7:
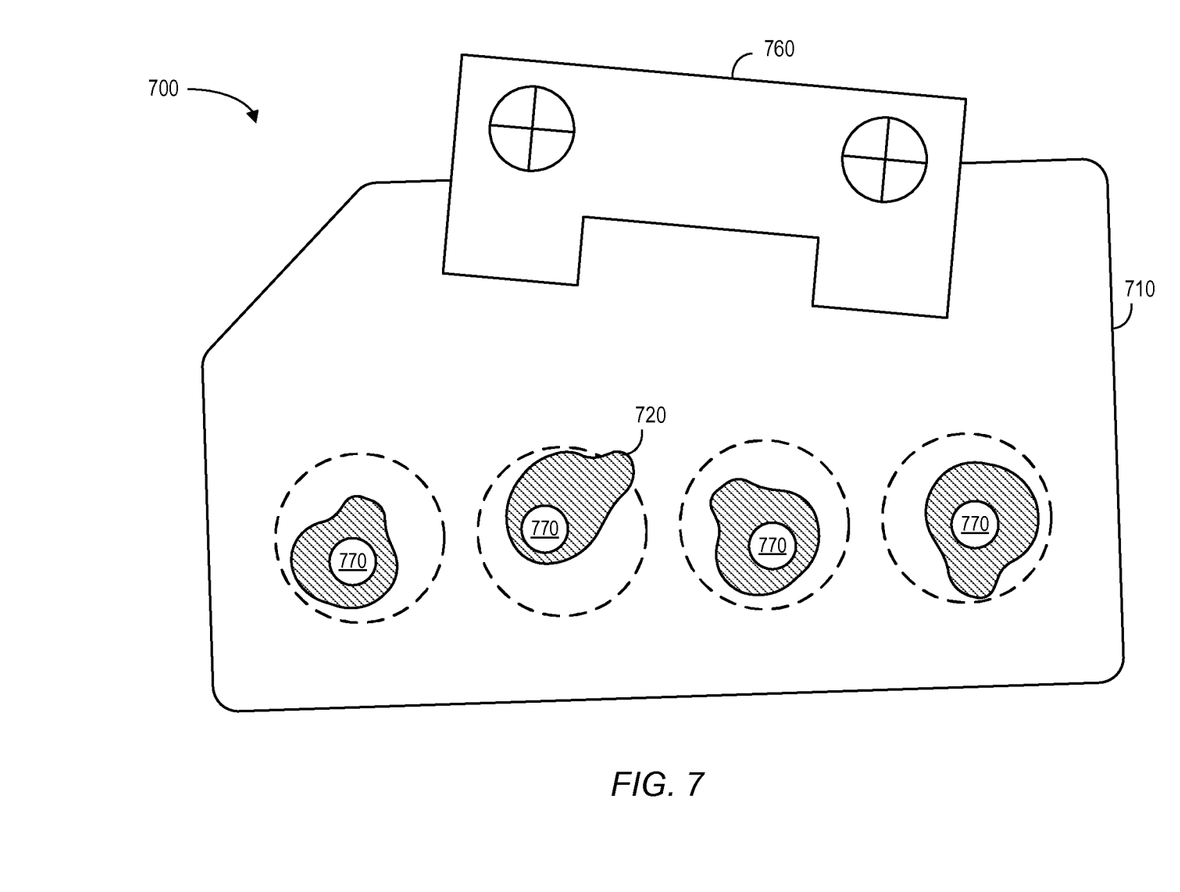
FIG. 7 illustrates a result of processing the image of FIG. 6 according to some embodiments.

In the example of FIG. 6, based on the image locations of the detected fiducial markings 662 in the image, a plurality of sampling regions of interest 630 within the image may be predicted. Moreover, within each sampling region of interest 630, the sample area 620 might be detected and a plurality of sample portions may be punched from these areas 620. For example, FIG. 7 illustrates 700 an FTA card 710 held by a gripping element 760. Moreover, as a result of the method described with respect to the processing example 600 of FIG. 6, sample portions have been removed through punching from the sample area 720, resulting in holes 770 in the FTA card 710. The separated sample portions may be tested according to some embodiments. That is, the separation of the four circular portions will create four corresponding circular holes 770 in the FTA card 710 (each having a biological sample). The four circular separated portions can be collected (e.g., in a tray of four vials) and sent to a laboratory for testing.

Figure 8:
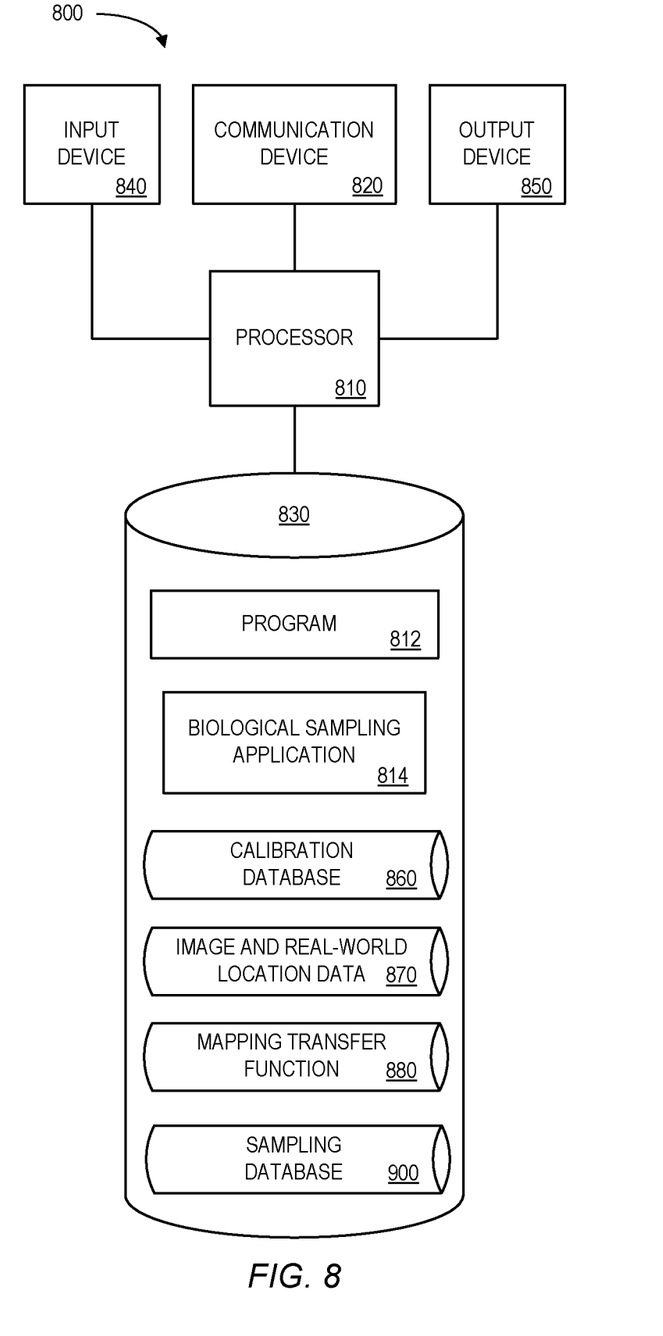
FIG. 8 is block diagram of a tool or platform according to some embodiments of the present invention.

The embodiments described herein may be implemented using any number of different hardware configurations. For example, FIG. 8 is block diagram of a tool or platform 800 that may be, for example, associated with the system 200 of FIG. 2. The automated sampling platform 800 comprises a processor 810, such as one or more commercially available Central Processing Units (CPUs) in the form of one-chip microprocessors, coupled to a communication device 820 configured to communicate via a communication network (not shown in FIG. 8). The communication device 820 may be used to communicate, for example, with one or more remote devices (e.g., to collect or transmit sampling data). The automated sampling platform 800 further includes an input device 840 (e.g., a computer mouse and/or keyboard to indicate that a card is ready to be sampled) and an output device 850 (e.g., a computer monitor to display reports).

The processor 810 also communicates with a storage device 830. The storage device 830 may comprise any appropriate information storage device, including combinations of magnetic storage devices (e.g., a hard disk drive), optical storage devices, mobile telephones, and/or semiconductor memory devices. The storage device 830 stores a program 812 and/or one or more biological fluid sampling applications 814 for controlling the processor 810. The processor 810 performs instructions of the programs 812, 814, and thereby operates in accordance with any of the embodiments described herein. For example, the processor 810 may receive an indication that a biological sample capture substrate is ready to be processed. An image of the sample capture substrate may be obtained by the processor 810, and a plurality of fiducial markings on a robot controller's gripping element may be automatically detected within the image. Based on image locations of the detected fiducial markings in the image and a mapping transfer function between detected image locations and real-world locations, the processor 810 may arrange for sample portions to be automatically taken from the sample capture substrate.

The programs 812, 814 may be stored in a compressed, uncompiled and/or encrypted format. The programs 812, 814 may furthermore include other program elements, such as an operating system, clipboard application a database management system, and/or device drivers used by the processor 810 to interface with peripheral devices.

As used herein, information may be "received" by or "transmitted" to, for example: (i) the automated sampling platform 800 from another device; or (ii) a software application or module within the automated sampling platform 800 from another software application, module, or any other source.

In some embodiments (such as shown in FIG. 8), the storage device 830 further stores a calibration database 860, an image and real-world location database 870, a mapping transfer function 880, and a sampling database 900. An example of a database that may be used in connection with the automated sampling platform 800 will now be described in detail with respect to FIG. 9. Note that the database described herein is only one example, and additional and/or different information may be stored therein. Moreover, various databases might be split or combined in accordance with any of the embodiments described herein. For example, the calibration database 860, the image and real-world location database 870, the mapping transfer function 880, and/or the sampling database 900 might be combined and/or linked to each other within the program 812 and/or the biological fluid sampling application 814.

Figure 9:
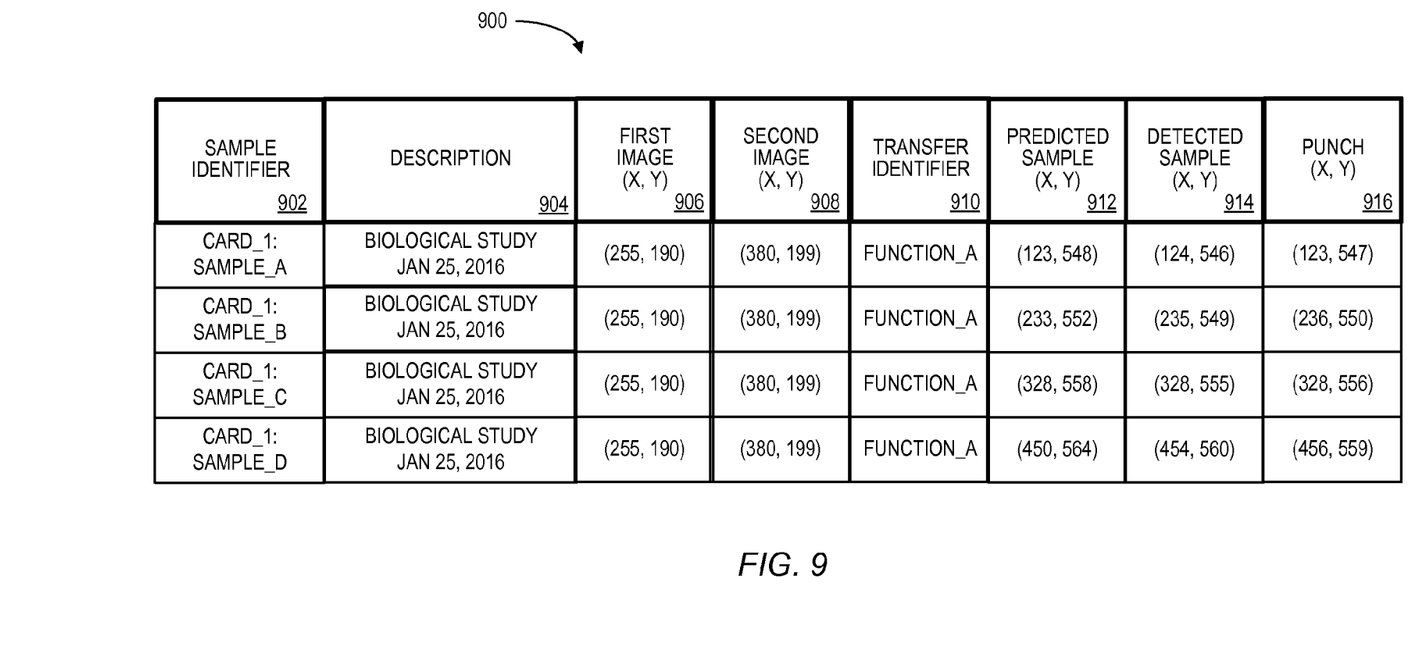
FIG. 9 is a tabular portion of a calibration database according to some embodiments.

Referring to FIG. 9, a table is shown that represents the sampling database 900 that may be stored at the automated sampling platform 800 according to some embodiments. The table may include, for example, entries identifying requests for resources that have been received. The table may also define fields 902, 904, 906, 908, 910, 912, 914, 916 for each of the entries. The fields 902, 904, 906, 908, 910, 912, 914, 916 may, according to some embodiments, specify: a sample identifier 902, a description 904, fiducial locations 96, 908, a transfer identifier 910, a predicted sample location 912, a detected sample location 914, and a punch location 916. The sampling database 900 may be created and updated, for example, when samples are processed.

The sample identifier 902 may be, for example, a unique alphanumeric code identifying an FTA card, a sample number, a date, etc. The description 904 might indicate why the sample was collected, who submitted the sample, etc. The first and second fiducial locations 906, 908 might be image pixel locations where a logo or crosshair marking on a gripping element was detected. The transfer identifier 910 might be associated with a mapping transfer function that was previously created during a calibration process (e.g., as described with respect to FIGS. 3 and 4). Based on the fiducial locations 906, 908 and the mapping function, a predicted sample location 912 may be automatically generated. The detected sample location 914 might represent where the sample was found, and the punch location 916 might indicate where the sample portion was actually punched on the FTA card.

Figure 10:
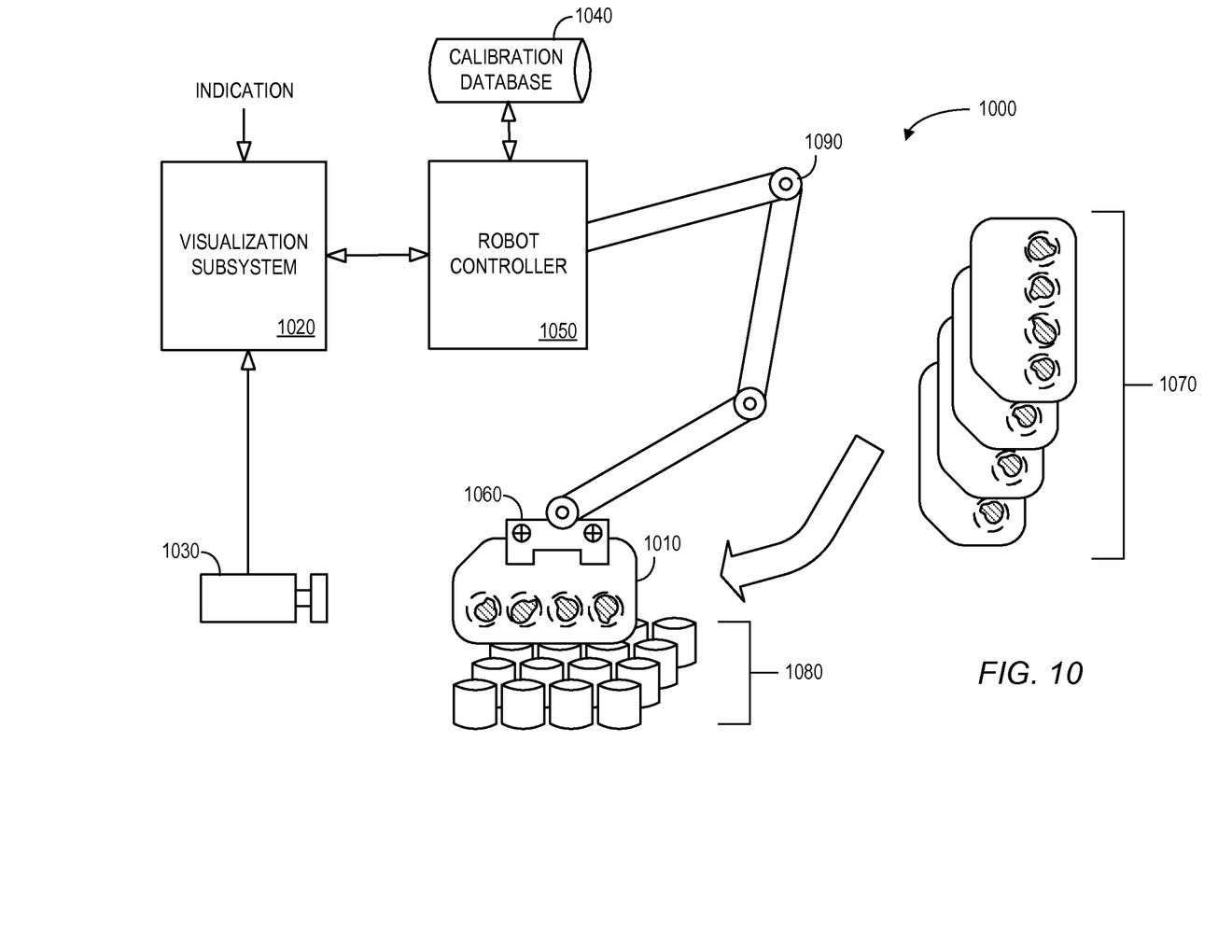
FIG. 10 illustrates an automated sample processing system in accordance with some embodiments.

FIG. 10 illustrates an automated sample processing system 1000 that may be used to analyze a sample capture substrate 1010 in accordance with some embodiments. The system includes a visualization subsystem 1020 having a camera 1030 able to capture image information. According to some embodiments, the visualization subsystem 1020 determines the position of the sample capture substrate 1010 within a gripping element 1060 and the positions of any prior punches on the sample capture substrate 1010. The camera 1030 might comprise, for example, a "smart camera" with a Charge-Coupled Device ("CCD") image sensor integrated with a processor in a package. Various processing and analysis described herein might, for example, be implemented directly on the embedded processor.

According to some embodiments, the camera 1030 may include two Ethernet ports, one connecting to a host computer where a graphical user interface displays real-time results, and the other to a robot controller 1050. A communication protocol may be configured so that the camera 1030 can serve as a closed-loop feedback device to the robot controller 1030. The camera 1030 may be prompted, according to some embodiments, via a Transmission Control Protocol ("TCP") instruction when a sample capture substrate 1010 is presented for inspection, triggering an image capture. The image may then be processed to recognize and locate standard position markers along with any prior punches to the sample capture substrate 1010. When complete, a message containing a positioning directive and list of available punching locations may be sent back via TCP to the robot controller 1050.

According to some embodiments, the visualization subsystem 1020 is programmed to recognize markers on the gripping element 1060, which may allow for automatic calibration of the punching system reference frame. This calibration may be robust to any in-plane camera 1030 movement. Moreover, the visualization subsystem 1020 may correct for variability of the sample capture substrate 1010 position within the gripping element 1060.

The robot controller 1050 may use a robot arm 1090 with the gripping element 1060 to pick up the sample capture substrate 1010 from a holder 1070 that contains multiple substrates 1010 and move the substrate 1010 into a field of view of the camera 1030. The robot arm 1090 may remove the sample capture substrate 1010 from the holder 1070, place it in front of the camera 1030 for imaging and punching, and return the sample capture substrate 1010 to the holder 1070. The robot arm 1090 might comprise, for example, a 6-axis robot arm with a smart gripping element 1060, such as the SG2.1-75MM-10N gripping element produced by Applied Robotics Inc. The system 1000 may include an on-board single axis controller for parallel gripping and the capability for standalone operation. In addition to controlling grip distance, speed, and velocity, the system 1000 may be programmed to do other tasks, such as detecting the presence of an object within its grasp and to modulate the grip force if necessary. The different gripping tasks (e.g., "open for card" and "grip card") may be controlled using a parallel communication protocol over digital input lines. Feedback may be indicated using individual digital output lines.

The gripping element 1060 for picking up card substrates 1010 might comprise, for example, two rectangular plates with six threaded holes in each plate for mounting setscrews with sharp ends. These setscrews may act as "teeth" to prevent the card substrate 1010 from slipping during handling.

According to some embodiments, the automated processing system 1000 may receive an indication that that sample capture substrate 1010 is ready to be processed. The indication may be received, for example, from a lab technician or directly from the robot controller. The visualization subsystem 1020 may store information in and/or retrieve a calibration database 1040. The calibration database 1040 may be locally stored or reside remote from the system 1000. Based on the information in the calibration database 1040, the visualization subsystem 1020 and robot controller 1050 may accurately punch holes in the sample capture substrate 1010 (and the resulting portions may be collected in an array of vials 1080 that automatically shifts when a new card is processed).

The system 1000 may facilitate an automated processing of biological samples in an efficient and accurate manner in accordance with any of the embodiments described herein. For example, one common step when processing dried blood spots on an FTA card is to cut out a 1 to 3 mm diameter disc from the areas where the blood spots are located. When an FTA card is processed with the automated system 1000, the system 1000 may initially identify the location of the blood (or other biological samples) on the card. This information may then be fed to a cutting or punching subsystem. According to some embodiments, an image of the card may be accurately translated into coordinates for the cutting subsystem according to any of the embodiments described here.

A closed-loop integration of the visualization subsystem 1020 to locate dried blood spots with the robot controller 1050 that performs a spot punching operation may be associated with a calibration method that maps pixel-based positions in the image from the camera 1030 to millimeter-based coordinates in the robot controller 1050 frame of reference, while accounting for any perspective distortion due to the camera's angle of sight to the viewed card. In addition, a card inspection procedure may wait for a prompt indicating that a card is presented for viewing, locate blood spots on the card, and communicate punching coordinates back to the robot controller 1050. The card inspection may be robust to disturbances in the camera 1030 placement, even when a disturbance has occurred after calibration. According to some embodiments, calibration is performed relatively infrequently. In some embodiments, calibration is performed once and repeated only if substantial changes occur to the relative placement of substrate 1010 and camera 1030.

According to some embodiments, the calibration procedure is accomplished in concert with the robot controller 1050, by first extracting a blank substrate from the card holder 1070 and punching out a three-by-three grid pattern according to a known set of robot frame coordinates. The card may then be presented for viewing and processing by the visualization subsystem 1020, which may locate the nine punch locations by predicting regions of interest fixed with respect to the locations of left and right fiducial markings on the gripping element 1060, which may themselves be located by means of a pattern matching process. The centers of the punch locations in pixels may be determined, for example, by inferring the centers of best-fitting circles. These centers may then be associated with corresponding robot controller 1050 frame positions, and a calibration mapping may be computed and stored in the calibration database 1040. The mapping may represent a transfer function between image pixels and robot controller 1050 frame coordinates that, when applied specifically to the grid points, yield minimum error to the true robot controller 1050 frame positions. The mapping may then be applied to the fiducial locations, yielding their true positions in the robot controller 1050 frame.

The fiducial locations on the gripping element 1060 may facilitate a main inspection procedure, which locates blood spots and may be robust to millimeter-scale disturbances in the relative placement of the gripping element 1060, the punching system, and the camera 1030. Inaccuracies in calibration may have a direct impact on the minimum spot that can be accurately punched, and may affect the proximity of successive punches when resampling of the same blood spot is desired. It should be noted that the mapping transfer function between the robot coordinate system and robot controller 1050 frame is established by the placement of both the gripping element 1060 and the punching system. When the fiducial markings are located in the "robot frame," their locations may also account for any disturbance in the punching system.

Thus, in some embodiments the system may only loosely know the locations of the punching system and the camera relative to the robot reference frame. When the calibration pattern is punched in the card, the puncher location may be determined relative to the fiducials on the gripper. If a normal calibration method was attempted (i.e., determine where the puncher is relative to the robot's workspace with some type of pointing tool, and then use that information with a camera calibration transform), this may require the robot to maintain high accuracy over the entire workspace (because the robot is in a different position for each sample punched). This approach may be undesirable because robots with a large workspace have good repeatability but typically lower absolute positional accuracy. In some embodiments described herein, an advantage may be obtained in that the puncher itself may be used to help calibrate its position. Once calibrated, the moves to the different sample positions are only incremental in nature, which help to maintain high positional accuracy. Furthermore, because an image before each punch is acquired with the gripper fiducials in view, embodiments may be very robust to a changes in camera positions. As a result, embodiments may tolerate significant camera positional errors in 4 degrees of freedom (x, y, z, and rotation normal to the image plane), with only the fiducials and the spots need to be in view. Also, because the calibration method utilizes the media of interest (the substrate cards), the calibration may be relatively simple and might be performed automatically if desired. Moreover, special tooling or tool changes may not be necessary.

Estimating the blood spot positions may comprise a self-correcting procedure based on the fiducial locations, whose positions in the image are permitted to vary for each inspection. During card inspection, visualization subsystem 1020 may again perform pattern matching to locate the fiducial markings, and apply the previously stored calibration mapping to express these locations in the robot controller 1050 frame. Using a combination of edge finding and circle fitting within the regions of interest, the visualization subsystem 1020 may perform similar position computations for any detected blood spots. Computed parameters comprising left fiducial position, angle to right fiducial, and number and positions of detected blood spots, may then be transmitted via TCP to the robot controller 1050.

The next step in blood-spot localization may, according to some embodiments, be performed by the robot controller 1050. The robot controller 1050 may receive the fiducial coordinates, subject to any prior camera 1030 motion, and compute a correction transformation modeling both translation and rotation effects. This correction may in turn be applied to all received spot locations, yielding the final coordinates for automated and accurate punching.

Thus, some embodiments described herein may provide the automated processing of biological fluid samples in an efficient and accurate manner.

The following illustrates various additional embodiments of the invention. These do not constitute a definition of all possible embodiments, and those skilled in the art will understand that the present invention is applicable to many other embodiments. Further, although the following embodiments are briefly described for clarity, those skilled in the art will understand how to make any changes, if necessary, to the above-described apparatus and methods to accommodate these and other embodiments and applications.

Although specific hardware and data configurations have been described herein, note that any number of other configurations may be provided in accordance with embodiments of the present invention (e.g., some of the information associated with the databases described herein may be combined or stored in external systems).

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

The invention claimed is:
1. A method associated with an automated biological sample processing system having a gripping element to hold biological sample capture substrates, the method comprising:
   receiving an indication that a biological sample capture substrate is ready to be processed;
   obtaining an image of the sample capture substrate;
   automatically detecting, within the image, a plurality of fiducial markings on the gripping element; and
   based on image locations of the detected fiducial markings in the image and a mapping transfer function between detected image locations and real-world locations, arranging for biological sample portions to be automatically taken from the sample capture substrate by the sample processing system, further comprising, prior to said receiving
   commanding the gripping element to move to a set of re-determined robot-frame locations, wherein a marking is punched into a calibration sample capture substrate at each location;
   obtaining a calibration image of the calibration sample capture substrate;
   automatically detecting, within the calibration image, the plurality of fiducial markings on the gripping element;
   based on image locations of the detected fiducial markings in the calibration image, predicting a set of calibration regions of interest within the calibration image;
   detecting the previously punched marking within each calibration region of interest; and
   automatically creating, by the sampling system, the mapping transfer function between detected image locations and real-world locations resulting front the commanded locations of the gripping element when the markings were punched.

2. The method of claim 1, wherein the sample capture substrate comprises a porous card.

3. The method of claim 1, wherein an applied biological fluid to the biological sample capture substrate comprises at least one of (i) blood, (ii) saliva, (iii) plant material, (iv) insect material, (v) viral material, (vi) bacterial material, (vii) genetic material, (viii) food, and (ix) animal biological fluid.

4. The method of claim 1, wherein said arranging comprises transmitting location information from a visualization subsystem to a robot controller associated with the gripping element.

5. The method of claim 4, wherein the robot controller is to punch a plurality of sample portions from the capture substrate leaving holes in the sample capture substrate.

6. The method of claim 5, wherein said arranging comprises:
   based on the image locations of the detected fiducial markings in the image, predicting a plurality of sampling regions of interest within the image; and
   detecting, within each sampling region of interest, a biological sampling area, wherein said plurality of sample portions are punched from within the biological sample areas.

7. The method of claim 1, wherein at least one of said detections are performed outside of the visible spectrum.

8. The method of claim 1, wherein the markings previously created on the calibration sample capture substrate comprise a matrix of punched holes.

9. A non-transitory, computer-readable medium storing instructions that, when executed by a computer processor, cause the computer processor to perform a method associated with an automated biological sample processing system having a gripping element to hold biological sample capture substrates, the method comprising:

receiving an indication that a biological fluid sample capture substrate is ready to be processed;

obtaining an image of the sample capture substrate;

automatically detecting, within the image, a plurality of fiducial markings on the gripping element; and based on image locations of the detected fiducial markings in the image and a mapping transfer function between detected image locations and real-world locations, arranging for biological sample portions to be automatically taken from the sample capture substrate by the sample processing system, further comprising, prior to said receiving;

commanding the gripping element to move to a set of pre-determined robot-frame locations, wherein a marking is punched into a calibration sample capture substrate at each location;

obtaining a calibration image of the calibration sample capture substrate;

automatically detecting, within the calibration image, the plurality of fiducial markings on the gripping element;

based on image locations of the detected fiducial markings in the calibration image, predicting a set of calibration regions of interest within the calibration image;

detecting the previously punched marking within each calibration region of interest; and automatically creating, by the sampling system, the mapping transfer function between detected image locations and real-world locations resulting from the commanded locations of the gripping element when the markings were punched.

10. The medium of claim 9, wherein the sample capture substrate comprises a porous card and an applied biological fluid to the porous card comprises at least one of: (i) blood, (ii) saliva, (iii) plant material, (iv) insect material, (v) viral material, (vi) bacterial material, (vii) genetic material, (viii) food, and (ix) animal biological fluid.

11. The medium of claim 9, wherein said arranging comprises transmitting location information from a visualization subsystem to a robot controller associated with the gripping element, and the robot contoller is to punch a plurality of sample portions in the sample capture substrate.

12. The medium of claim 11, wherein said arranging comprises:

based on the image locations of the detected fiducial markings in the image, predicting a plurality of sampling regions of interest within the image; and detecting, within each sampling region of interest, a biological sample area, wherein said plurality of sample portion are punched within the biological sample areas.

13. The medium of claim 9, wherein the markings previously created on the calibration sample capture substrate comprise a matrix of punched holes.

14. An automated biological sample processing system, comprising:

a visualization subsystem having a camera to capture images;

a robot having a gripping element to hold biological sample capture substrates; and a robot controller, coupled to the visualization subsystem and the robot; and a computer system associated with at least one of the visualization subsystem and the robot controller to perform a method, the method comprising:

receiving an indication that a biological sample capture substrate is ready to be processed;

obtaining an image of the sample capture substrate;

automatically detecting, within the image, a plurality of fiducial markings on the gripping element; and based on image locations of the detected fiducial markings in the image and a mapping transfer function between detected image locations and real-world locations, arranging for biological sample portions to be automatically taken from the sample capture substrate, wherein the method further comprises, prior to said receiving;

commanding the gripping element to move to a set of pre-determined robot-frame locations, wherein a marking is punched into a calibration sample capture substrate at each location;

obtaining a calibration image of the calibration sample capture substrate;

automatically detecting, within the calibration image, the plurality of fiducial markings on the gripping element;

based on image locations of the detected fiducial markings in the calibration image, predicting a set of calibration regions of interest within the calibration image;

detecting the previously punched marking within each calibration region of interest; and automatically creating, by the sampling system, the mapping transfer function between detected image locations and real-world locations resulting from the commanded locations of the gripping element when the markings were punched.

15. The system of claim 14, wherein the sample collection substrate comprises porous card and a biological fluid applied to the porous card comprises at least one of (i) blood, (ii) saliva, (iii) plant material, (iv) insect material, (v) viral material, (vi) bacterial material, (vii) genetic material, (viii) food, and (ix) animal biological fluid.

16. The system of claim 14, wherein said arranging comprises transmitting location information from a visualization subsystem to the robot controller associated with the gripping, element, and the robot controller is to punch a plurality of sample portions in the sample capture substrate.

17. The system of claim 16, wherein said arranging comprises:

based on the image locations of the detected fiducial markings in the image, predicting a plurality of sampling regions of interest within the image; and detecting, within each sampling region of interest, a biological sample area, wherein said plurality of sample portions are punched within the biological sample areas.

18. The system of claim 14, wherein the markings previously created on the calibration sample capture substrate comprise a matrix of punched holes.

* * * * *